United States Patent
Gu et al.

(10) Patent No.: US 9,499,667 B2
(45) Date of Patent: Nov. 22, 2016

(54) BIODEGRADABLE SURFACTANT, PREPARATION METHOD AND USE THEREOF

(71) Applicants: GAINIA (SHANGHAI) PATENT TECHNOLOGY LTD., Shanghai (CN); POLYMER CHEMICAL CO. LTD, Shanghai (CN)

(72) Inventors: Xiaojun Gu, Shanghai (CN); Xin Teng, Shanghai (CN)

(73) Assignees: GAINIA (SHANGHAI) PATENT TECHNOLOGY LTD., Shanghai (CN); POLYMER CHEMICAL CO. LTD, Shanghai (CN)

( * ) Notice: Subject to any disclaimer, the term of this patent is extended or adjusted under 35 U.S.C. 154(b) by 0 days.

(21) Appl. No.: 14/762,763

(22) PCT Filed: Apr. 19, 2013

(86) PCT No.: PCT/CN2013/000453
§ 371 (c)(1),
(2) Date: Jul. 22, 2015

(87) PCT Pub. No.: WO2014/169403
PCT Pub. Date: Oct. 23, 2014

(65) Prior Publication Data
US 2015/0361219 A1    Dec. 17, 2015

(51) Int. Cl.
| | | |
|---|---|---|
| *A61K 47/34* | (2006.01) | |
| *C08G 73/02* | (2006.01) | |
| *A61K 47/48* | (2006.01) | |
| *C08G 63/08* | (2006.01) | |
| *C08G 63/664* | (2006.01) | |
| *C08G 65/48* | (2006.01) | |
| *C08G 63/685* | (2006.01) | |

(52) U.S. Cl.
CPC ....... *C08G 73/024* (2013.01); *A61K 47/48215* (2013.01); *C08G 63/08* (2013.01); *C08G 63/664* (2013.01); *C08G 63/6852* (2013.01); *C08G 65/48* (2013.01)

(58) Field of Classification Search
CPC . A61K 38/00; A61K 47/48215; C08G 63/08
See application file for complete search history.

(56) References Cited

U.S. PATENT DOCUMENTS

2012/0121711 A1* 5/2012 Hu .................. A61K 9/5153
                                              424/489

FOREIGN PATENT DOCUMENTS

| CN | 102219892 A | 10/2011 |
|---|---|---|
| WO | WO 2011/011978 A1 | 2/2011 |

OTHER PUBLICATIONS

Han et al, "Preparation of PLA-mPEG Block Copolymer Micelle and Their Surface Tension," Chinese Journal of Applied Chemistry, 2005, p. 403-406, vol. 22, No. 4.

* cited by examiner

*Primary Examiner* — Gregory Listvoyb
(74) *Attorney, Agent, or Firm* — Muncy, Geissler, Olds & Lowe, P.C.

(57) ABSTRACT

The invention provides a methoxypoly(ethylene glycol)-poly(lactide) block copolymer capped with phenylalanine group. The block copolymer is represented by formula (I), wherein R is acyl amine group, a=20-200, b=5-50; and molecular weights of the ethoxypoly(ethylene glycol) block component and the poly(lactide) block component respectively range from 1000-5000 and 1000-10000. The preparation method and use of the block copolymer are also provided.

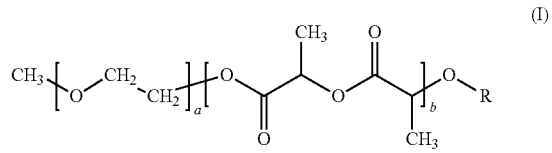

8 Claims, 6 Drawing Sheets

BIODEGRADABLE SURFACTANT, PREPARATION METHOD AND USE THEREOF

FIELD OF THE INVENTION

The present invention belongs to the technical field of biodegradable materials, which relates to a biodegradable copolymer, the preparation method and its uses in surfactant. In particular, the present invention relates to a methoxypoly(ethylene glycol)-poly(lactide) block copolymer capped with amino acid group, the preparation method and its uses.

BACKGROUND OF THE INVENTION

Surfactant is generally defined by containing both hydrophilic group (head) and hydrophobic group (tail) which has an orientation to form aggregates or micelles in aqueous solutions. The amphiphilic properties of surfactant significantly lower the surface tension or interfacial tension between two liquids or between a liquid and a solid material. Owing to their functional properties resulted by chemical and physical actions, such as wetting, anti-sticking, emulsifying/demulsifying, foaming/defoaming, solubilizing, dispersing, cleaning, antiseptic, and antistatic, surfactants are applied extensively and practically, and thus become a fine chemical engineering agent with diversified usability.

Surfactants have been developed for more than a half century. Surfactants were initially used for detergents, and they are applied in all fields of fine chemical engineering nowadays. Surfactants are developed rapidly in cosmetic industry, and become the most important component of cosmetic ingredients, which play crucial roles in cosmetics including the formulation, the manufacture, the carriage, and the usage. In order to obtain ideal performance of cosmetics consistently to finally satisfy the sensory demands of customers, people have to control the parameters of rheological property critically.

However, most of current surfactants irritate skins to a varying extent, and even cause acute symptoms of skin allergies. The dissolution, infiltration and reactivity of surfactants can induce mucosal irritation; and it is generally accepted that the direct cause is the infiltrated residues of the surfactants. A. Mehling and colleagues have studied the ocular and dermal (skin) irritation potential of surfactants by using various methods such as the red blood cell test, the hen's egg test-chorioallantoic membrane (HET-CAM), the Skinethic ocular tissue model, and 24 h epicutaneous patch test (ECT). The results indicate that coco-glucoside, lauryl D-glucoside, lauryl glucose carboxylate, sodium dodecyl-poly(oxyethylene) sulfate, sodium lauryl sulfate, ammonium lauryl sulfate, and other tested irritant surfactants can potentially cause mild, moderate, or even severe irritation.

Chlorinated organic surfactants and phenolic surfactants may cause defects in fetus and tumor formation in animal models. For example, sodium dodecyl benzene sulfonate can be absorbed dermally (through skin) to cause chronic symptoms such as liver lesion and splenic atrophy, and those surfactants are teratogenic and carcinogenic.

Low molecular polyethylene oxide belongs to nonionic surfactant, which is considered to be mutagenic and thus brings up safety concerns. For example, when conducting addition reaction with ethylene oxide (EO), excessive ethylene oxide results in unreacted ethylene oxide, low molecular polyethylene and 1,4-dioxane cyclized by diethyl dioxide.

In addition to the potential hazard through skin contact, surfactants can be environmentally hazardous because the surfactants are discharged down the drain with the dirty wash water. The bio-safety concerns of various surfactants widely used today including nonylphenol ethoxylate (NPE), diethanolamine (DEA) and linear alkylbenzene/linear alkylbenzene sulfonate (LAB/LAS) are existing unsolved problems. According to the current European standard, environmentally-safe surfactants are required to have 90% of average biodegradability, and 80% of initial biodegradability.

In view of above, the awakened public environmental consciousness and the heightened bio-safety criteria make cosmetic industry to choose the surfactant cautiously. It is observed that the issues of regulation and environmental protection increasingly limit the development of surfactants, which impacts significantly on the cosmetic industry supplying products applied to human body.

Therefore, people are seeking surfactants of low dermal irritancy, non-toxicity (including teratogenicity, mutagenicity and carcinogenicity), and biodegradability.

SUMMARY OF THE INVENTION

An aspect of the present invention is to provide a surfactant which is structurally capped with amino acid, and therefore the surfactant according to the present invention can be widely applied to replace the current commercial surfactants.

In order to accomplish the above aspect, the present invention provides a block copolymer having a methoxypoly(ethylene glycol) block component and a poly(lactide) block component; and the block copolymer is capped with an amino acid group and is represented by formula (I) below:

In formula I, R represents an acyl amine group, a is an integer of 11-455, preferably 20-200; and b is an integer of 3-300, preferably 5-50; the average molecular weight of the block copolymer ranging from 1000-70000, preferably from 2000-20000; the average molecular weight a methoxypoly(ethylene glycol) block component ranging from 500-20000, preferably from 1000-5000; and the average molecular weight a poly(lactide) block component ranging from 500-50000, preferably from 1000-10000.

According to one embodiment of the present invention, R of the block copolymer as previously described is represented by formula (II) below:

wherein $R_1$ is H, $CH_3$, $(CH_3)_2CH$, $PhCH_2$, or $(CH_2)_3NHC(NH)NH_2$.

According to one preferable embodiment of the present invention, $R_1$ of the block copolymer as previously described is $PhCH_2$ or $(CH_2)_3NHC(NH)NH_2$.

Another aspect of the present invention is to provide a method of preparing a block copolymer represented by formula (I) as described previously, wherein R represents an acyl amine group, a is an integer of 11-455, preferably 20-200; and b is an integer of 3-300, preferably 5-50; the average molecular weight of the block copolymer ranging from 1000-70000, preferably 2000-20000; the average molecular weight a methoxypoly(ethylene glycol) block component ranging from 500-20000, preferably 1000-5000; and the average molecular weight a poly(lactide) block component ranging from 500-50000, preferably 1000-10000.

The method includes the steps of: dissolving a methoxypoly(ethylene glycol)-poly(lactide) block copolymer and an amino acid in distilled water to form a working solution; adding a condensing agent into the working solution for reaction at room temperature for 4 to 48 hours to obtain a product solution; filtering the product solution to obtain a filtrate; extracting the filtrate by using a polar organic solvent and precipitating the filtrate by a non-polar organic solvent to obtain a precipitation; and drying the precipitation to obtain the final product. The molar ratio of the methoxypoly(ethylene glycol)-poly(lactide) block copolymer:amino acid:condensing agent ranges from 1:1-10:0.1-10, preferably from 1:1-3:0.1-1.

According to one embodiment of the present invention, the condensing agent is 3-(ethyliminomethyleneamino)-N,N-dimethyl-propan-1-amine (EDC).

According to one embodiment of the present invention, $R_1$ of the block copolymer as previously described is represented by formula (II) is H, $CH_3$, $(CH_3)_2CH$, $PhCH_2$, or $(CH_2)_3NHC(NH)NH_2$.

According to one preferable embodiment of the present invention, $R_1$ of the block copolymer as previously described represented by formula (II) is $PhCH_2$ or $(CH_2)_3NHC(NH)NH_2$.

According to one embodiment of the present invention, the methoxypoly(ethylene glycol)-poly(lactide) block copolymer can be prepared by the method includes the steps of: adding methoxypoly(ethylene glycol) and D,L-Lactide together into a dry flask, wherein the weight ratio of methoxypoly(ethylene glycol) to D,L-Lactide is 1:1; adding 0.1 g/mL of stannous octoate dissolved in dichloromethane into the flask, wherein the weight of the stannous octoate dissolved in dichloromethane is 1/2000-1/500 to the weight of either methoxypoly(ethylene glycol) or D,L-Lactide to form a reaction mixture; heating the reaction mixture to 80-100° C. to dissolve the methoxypoly(ethylene glycol); stirring and vacuuming the reaction mixture for at least an hour, during which the atmosphere is replaced with nitrogen alternatively for 3 times; sealing the flask in vacuum to perform a polymerization reaction at 130-150° C. in oil bath for 3.5-24 hours; cooling the mixture and breaking the sealed flask to obtain a solid; dissolving the solid with dichloromethane to form a crude solution, precipitating the crude solution with diethyl ether and filtering to obtain a precipitate; and drying the precipitate to obtain the desired block copolymer.

According to one embodiment of the present invention, the molar ratio of the previously described methoxypoly(ethylene glycol)-poly(lactide) block copolymer:amino acid:condensing agent ranges from 1:3:1.

According to one embodiment of the present invention, the previously described polar organic solvent is selected from the group consisting of dichloromethane, methanol, chloroform and tetrahydrofuran, wherein dichloromethane is preferable.

According to one embodiment of the present invention, the previously described non-polar organic solvent is selected form the group consisting of diethyl ether, petroleum ether and n-hexane, wherein diethyl ether is preferable.

Another object of the present invention is providing the use of the previously described methoxypoly(ethylene glycol)-poly(lactide) block copolymer capped with amino acid group for a surfactant.

Still another aspect of the present invention is providing a methoxypoly(ethylene glycol)-poly(lactide) block copolymer characterized in that the block copolymer is represented by formula (I) below:

wherein R represents an 2-amino-3-phenylpropanal group; a represents the number of the methoxypoly(ethylene glycol) block component and is an integer of 11-455, preferably 20-200; b represents the number of the poly(lactide) block component and is an integer of 3-300, preferably 5-50; the average molecular weight of the block copolymer ranges from 1000-70000, preferably from 2000-20000. The block copolymer has at least three peaks in a $^1$H-NMR measurement corresponding to the methoxypoly(ethylene glycol) block component, the poly(lactide) block component and the 2-amino-3-phenylpropanal group, including one peak corresponding to the methoxypoly(ethylene glycol) block component at a signal position of from 3.5 to 4 ppm, two peaks corresponding to the poly(lactide) block component at two signal positions of from 1 to 2 ppm and 5 to 5.5 ppm respectively, and three peaks corresponding to the 2-amino-3-phenylpropanal group at three signal positions of from 7 to 7.5 ppm, 3 to 3.5 ppm, and 4.5 to 5 ppm respectively.

The present invention does not limit the amino acid used to cap the block copolymer, and any type and grade of amino acid can be used.

The present invention does not limit the source of agents and solvents, and any type and grade of commercial agent and solvent can be used.

Compared to current techniques, the present invention provides a material having the following advantages and benefits: the present invention provides a material having better performance on the environmental compatibility, the non-toxicity, and the degradability compared to other types of chemically synthesized surfactants; and therefore it is more environmentally friendly. Compared to the conventional MPEG-PLA materials, the present invention provides a material with better biocompatibility, and this advantage is particularly significant when the material is used in high concentration, which means the material according to the present invention is an ideal choice for daily personal body care products. Compared to the conventional diblock copolymer, the triblock copolymer according to the present invention is capable of carrying more encapsulated ingredients. Therefore, more diverse or enriched functional ingredients can be added to the daily personal care products by using the material according to the present invention; and it ultimately enhances the market competitiveness of those products.

DETAILED DESCRIPTION OF THE INVENTION

Other characteristics and advantages of the invention appear more clearly on reading the following description given by way of non-limiting example and made with reference to the accompanying drawings.

Except as expressly specified in the description, the technical terms are defined as below.

The "amino acid" is generally defined as an organic compound having amine group and carboxylic acid functional group. Specifically, there are approximately 20 common amino acids for human body including, but not limited to, glycine, alanine, valine, leucine, isoleucine, serine, threonine, aspartic acid, asparagine, glutamic acid, glutamine, arginine, lysine, histidine, cysteine, methionine, phenylalanine, tyrosine, tryptophan, proline.

Amino acids are the unit molecule of bio-functional protein macromolecules as well as the nutrition source. Amino acids are readily available and are safe to use.

The amino acid group described in the present invention is defined as a functional group derived from the corresponding amino acid, and the simplified formula can be represented and as formula (II) below:

(II)

Formula (II) also represents an acyl amine group, and $R_1$ is selected from the group of H, $CH_3$, $(CH_3)_2CH$, $PhCH_2$, or $(CH_2)_3NHC(NH)NH_2$. More specifically, when $R_1$ is H, the amino acid group of the block copolymer is glycine (Gly or G); when $R_1$ is $CH_3$, the amino acid group of the block copolymer is alaine (Ala or A); when $R_1$ is $(CH_3)_2CH$, the amino acid group of the block copolymer is valine (Val or V); when $R_1$ is $PhCH_2$, the amino acid group of the block copolymer is phenylalanine (Phe or F); and when $R_1$ is $(CH_2)_3NHC(NH)NH_2$, the amino acid group of the block copolymer is arginine (Arg or R).

The "block copolymer" described in the present invention means copolymers comprise two or more homopolymer subunits linked by covalent bonds. The block copolymer integrates the advantageous properties of various polymers to obtain a more excellent functional polymer material. The block copolymer has the characteristics of: controllable molecular weight, narrower distribution of molecular weight, designable molecular structure with desired block component. Besides, the specific structure of a block polymer usually gives the block polymer a simple linear conformation and other distinguishable characteristics from the random copolymers and the mixture of homopolymers. Therefore, it broadens the applications of block polymers in biomedical, architectural, and chemical engineering fields.

The "polar organic solvent" described in the present invention means solvents having significant charge polarity, including, but not limited to: dichloromethane, ethyl acetate, chloroform, and tetrahydrofuran (THF). The "non-polar organic solvent" described in the present invention means solvents having no significant charge polarity, including, but not limited to: ethyl ether, n-hexane, and cyclohexane.

The "condensing agent" described in the present invention means the catalysts for the esterification reactions, which catalyze those reactions, including, but not limited to: dicyclohexylcarbodiimide (DCC), 1-(3-dimethylaminopropyl)-3-ethylcarbodiimide hydrochloride (EDC), concentrated sulfuric acid, concentrated hydrochloric acid, 4-methylbenzenesulfonic acid (PTSA) and sulfurous dichloride ($SOCl_2$).

The "room temperature" described in the present invention is also described as ordinary temperature or normal temperature, and the actual temperature depends on environment. Generally, the room temperature means the typical or preferred indoor temperature, denoting the small range of temperatures, approximately 25° C. or 300K (about 27° C.) for absolute temperature.

Except as expressly specified in the description, all reagents and materials used in the experiments or embodiment examples are commercially available from normal market.

In one preferred embodiment of the present invention, methoxypoly(ethylene glycol), also called MPEG has excellent solubility in aqueous environment, capability of wetting, lubricity; and it is biologically inert and irritant-free to human body. With these mild characteristics, methoxypoly(ethylene glycol) is widely used in cosmetic industry and pharmaceutical industry. Variously graded types methoxypoly(ethylene glycol) are utilized to modify the viscosity, hygroscopicity, and structure of the end product. Methoxypoly(ethylene glycol) products with relatively low molecular weight (e.g., molecular weight <2000) are suitably used as wetting agents and pasting agents for modifying the consistency; and therefore, those low-molecular products are widely used in manufacturing ointment, cream, lotion, toothpastes, shaving cream, and so on. Methoxypoly(ethylene glycol) products with relatively high molecular weight are suitably used in manufacturing lipstick, deodorant, soap, shaving cream, foundation cream, various cosmetics, and so on. When being used in manufacturing detergents, those high-molecular products are used as suspending agents and thickening agents. When being used in pharmaceutical industry, those high-molecular products are used as a groundmass of emulsion, balm, ointment, cleaning agent and suppository

In one preferred embodiment of the present invention, poly lactic acid (PLA), also called poly(lactide), is a polymer derived from lactic acids. Poly lactic acid becomes a group of "green polymers" based on the following advantages: the source of the poly lactic acids is naturally abundant; the poly lactic acid is renewable; the manufacturing processes of the poly lactic acid are usually pollution-free; the product polymers are biodegradable; as well as other excellent properties including ideal biocompatibility, glossiness, transparency, feel in operation, and heat endurance. Poly lactic acid is characteristic of excellent compatibility and degradability, it is widely applied in medical and pharmaceutical field, for example, poly lactic acid is used to manufacture disposable infusion devices for a single use, bio-absorbable suture; and the low-molecular poly lactic acid is used as a slow-releasing drug carrier.

The present invention provides a methoxypoly(ethylene glycol)-poly(lactide) block copolymer capped with an amino acid group. The block copolymer has a methoxypoly (ethylene glycol) block component and a poly(lactide) block component, it is represented by formula (I) below:

According to the formula (I), R represents an acyl amine group, a represent the number of the methoxypoly(ethylene glycol) block component, and a is an integer of 11-455, preferably 20-200; and b represent the number of the poly (lactide) block component and b is an integer of 3-300, preferably 5-50; the average molecular weight of the block copolymer ranging from 1000-70000, preferably from 2000-20000; the average molecular weight a methoxypoly(ethylene glycol) block component ranging from 500-20000, preferably from 1000-5000; and the average molecular weight a poly(lactide) block component ranging from 500-50000, preferably from 1000-10000.

Preferably, R is represented by represented by formula (II):

Preferably, $R_1$ of the formula (II) is H, $CH_3$, $(CH_3)_2CH$, $PhCH_2$, or $(CH_2)_3NHC(NH)NH_2$. Different R is derived from different amino acids of distinguish features, such as non-polar amino acids (glycine, alanine, Valine and phenylalanine) and basic amino acid (arginine).

EXAMPLE 1

Preparation of a block copolymer capped with an amino acid group. Specifically, according to one embodiment of the present invention, the amino acid used is phenylalanine, and thus the amino acid capping the block copolymer is derived from phenylalanine. The block copolymer product according to Example 1 is called MPEG-PLA-Phe hereinafter.

Add 10 g of methoxypoly(ethylene glycol) (hereinafter "MPEG") with molecular weight of 2000, 15 g of D,L-Lactide, 0.15 mL stannous octoate dissolved in dichloromethane into a dry polymerization flask. Heat the mixture to 80° C. and drying under vacuum for 5 hours and then seal the polymerization flask. Perform the polymerization reaction at 130° C. for 15 hours, and then break the polymerization flask to obtain a solid. Dissolve the solid with dichloromethane to form the crude solution. Precipitate the crude solution with diethyl ether. Repeat the dissolving and precipitating step as previously described for 3 times to obtain the methoxypoly(ethylene glycol)-poly(lactide)(hereinafter "MPEG-PLA"). The molecular weight of MPEG-PLA ranges from 200-20000.

Weigh and dissolving 4 g of MPEG-PLA, 0.495 g of L-phenylalanine, 0.19 g of condensing agents EDC (molar ratio is 1:3:1) in 50 mL distilled water. Adjust the pH value to 5.0 by using hydrochloric acid, and conduct the reaction at room temperature for 36 hours. Extract the reacted solution by 50 ml dichloromethane repeatedly for 3 times, pool the organic phase and remove partial volume of the solvent, then precipitate the residual reacted solution by ethyl ether to obtain white solid, which is the desired product of MPEG-PLA-Phe. The yield is 4.02 g (96.5%).

The desired product of MPEG-PLA-Phe is characterized by nuclear magnetic resonance spectroscopy (NMR), infrared spectroscopy (IR) and gel permeation chromatography (GPC) methods, to determine their physical properties including spatial structure, monocular weight, and polydispersity. The results of structural characteristics of the desired product are respectively shown in FIGS. 1 and 2.

Figure 1:
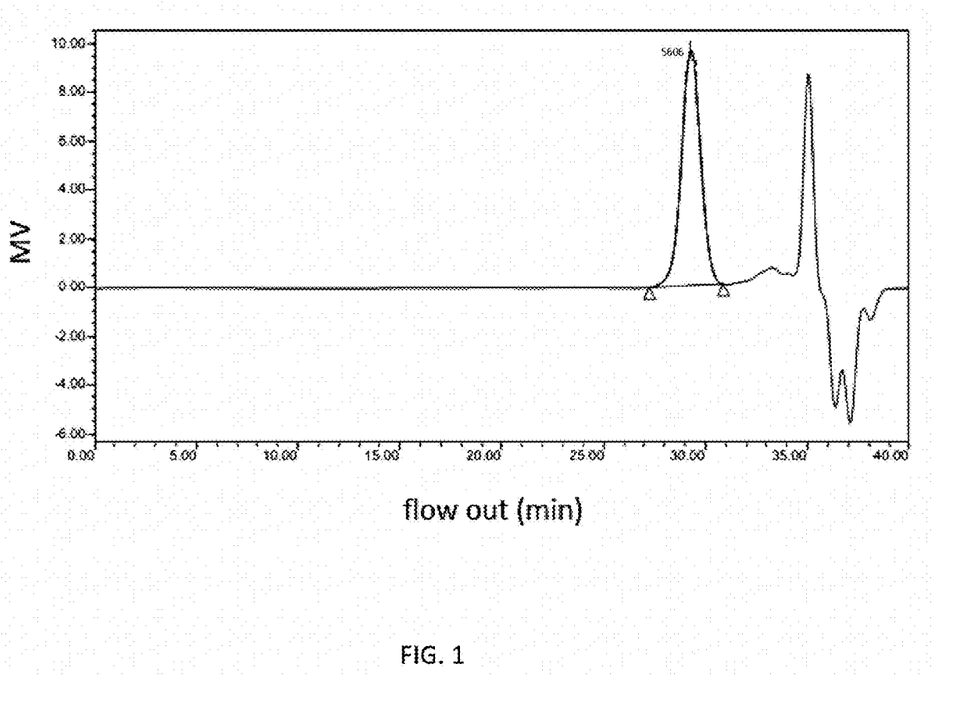
FIG. 1 is a gel permeation chromatography (GPC) chromatogram showing the distribution and the molecular weight of the block copolymer according to Example 1. The polydispersity index (PDI) is 1.05 and the peak shape is nearly symmetrical; both indicate excellent purity of the block copolymer.

According to the GPC results, the polydispersity index (PDI) of the desired product is 1.05 and the peak shape is nearly symmetrical, and those features indicate that the purity of the desired product is excellent.

Figure 2:
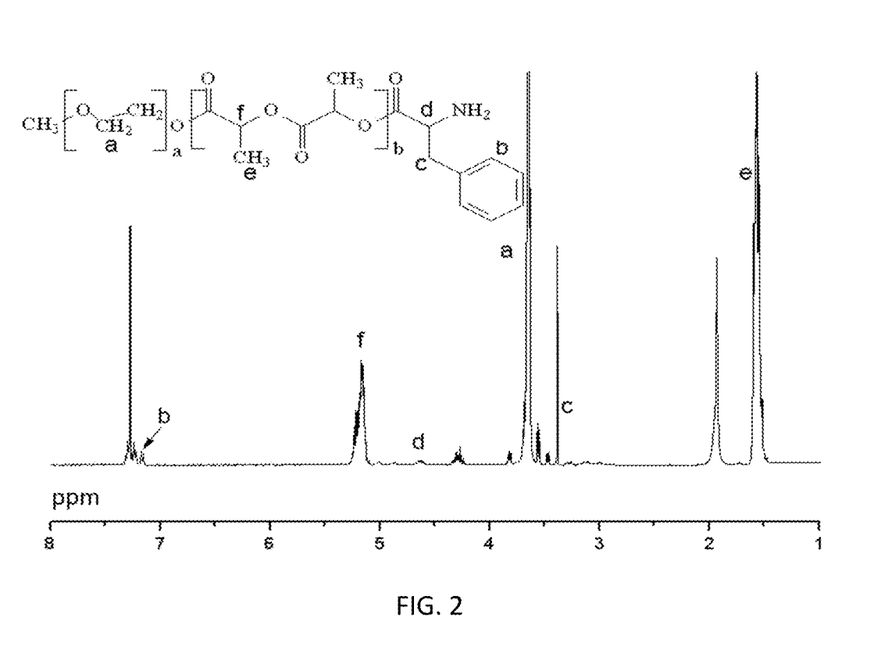
FIG. 2 shows H1 NMR spectrum of the block copolymer according to Example 1.

The desired product of Example 1 is a specific methoxypoly(ethylene glycol)-poly(lactide) block copolymer. The structural features of the block copolymer are determined by NMR and the results are shown in FIG. 2. Specifically, the $H^1$-NMR is applied for characterization, and the details related to this method are well-known in the field of the present invention; thus the procedure of the method is not detailed herein. In brief, the structural features are characterized primarily by parameters of the chemical shift and the coupling constant. The chemical shift reflects the specific electronic environment of the resonating nuclei, and the resultant resonance frequency is profiled by the different absorption peak in the $H^1$-NMR spectrum. The difference between absorption peaks (hereinafter "peak") is reflected by chemical shift, usually expressed in parts per million (ppm), and is calculate by specific equation. The coupling constant affects significantly the shape of peak, for example, a multi-peak profile usually relates to the interaction of different functional groups. The coupling constant reflects the level of spin coupling and provides information on the connectivity of molecules. The coupling constant is usually represented by "J" and expressed in hertz (Hz).

To analyze NMR data, the intensity of the peak provides key information. Specifically, the atomic nucleus in the same electronic environment will be reflected by the same peak in NMR spectrum, and the intensity of the peak (calculated by integration) is analyzed to estimate the number of the nucleus, and ultimately unveils the structure of the assayed molecules.

Refer to FIG. 2 showing the result of the structural characteristics of the desired product according to Example 1. Peaks attributing to the same component of the block polymer is indicated by the same symbol (a, b, c, d, e, f), and the peaks are described expressly by chemical shift in the unit of ppm: the peak "a" at a signal position of from 3.5 to 4 corresponds to the methoxypoly(ethylene glycol) block component; the peak "e" and "f" respectively at signal positions of from 1 to 2 represent and from 5 to 5.5 corresponds to poly(lactide) block component; and the peak "b", "c", and "d" respectively at signal positions of from 7 to 7.5, from 3 to 3.5 and from 4.5 to 5 corresponds to the phenylalanine component. However, according to other embodiments of the present invention, the peaks of chemical shift as well as the peak shape will correspondingly change in accordance with the number of methoxypoly(ethylene glycol) block component, the number of poly(lactide) block component and the different amino acid group. These peak characteristics are used to feature other block copolymers obtained according to other embodiments of the present invention.

To examine the surfactant property, add 60 mL water and 8 mL hexadecane into a 12-cm culture dish, and the hexadecane spreads and forms an oil film on the surface of water. Dissolve the quantified product of Example 1 in water to form a 30% of aqueous solution and then drop this solution into the center of the hexadecane oil film. It's observe that the oil spreads toward radially. This phenomenon demonstrates that the product obtained according to Example 1 has the feature of surfactant.

The product obtained according to Example 1, methoxypoly(ethylene glycol)-poly(lactide) block copolymer capped with phenylalanine group, is further used to determine the cytotoxicity by using a colorimetric assay for assessing cell viability and growth. This assay is based on the colorimetric feature of (3-(4,5-Dimethylthiazol-2-yl)-2,5-diphenyltetrazolium bromide), also called MTT or thiazolyl nlue tetrazolium bromide, which is widely used in vitro for determine whether a stimuli (e.g., medicinal agents and radiation). The principle is based on that the succinate dehydrogenase in live cells can reduce the exogenous MTT to form insoluble formazan with blue or purple appearance and then the formazan deposits inside the cells; while dead cells have no reduction activity. Dimethyl sulfoxide (DMSO) can dissolve the formazon deposited inside the cells, and the amount of dissolved formazon can be measured by detecting the optical density (OD) at specific absorbance using the colorimetric meter or ELISA Reader, which reflects the quantities of live cells. More intense the OD value represents better activity of live cells, which means the stimuli or the tested agent is less toxic to cells.

Figure 3A:
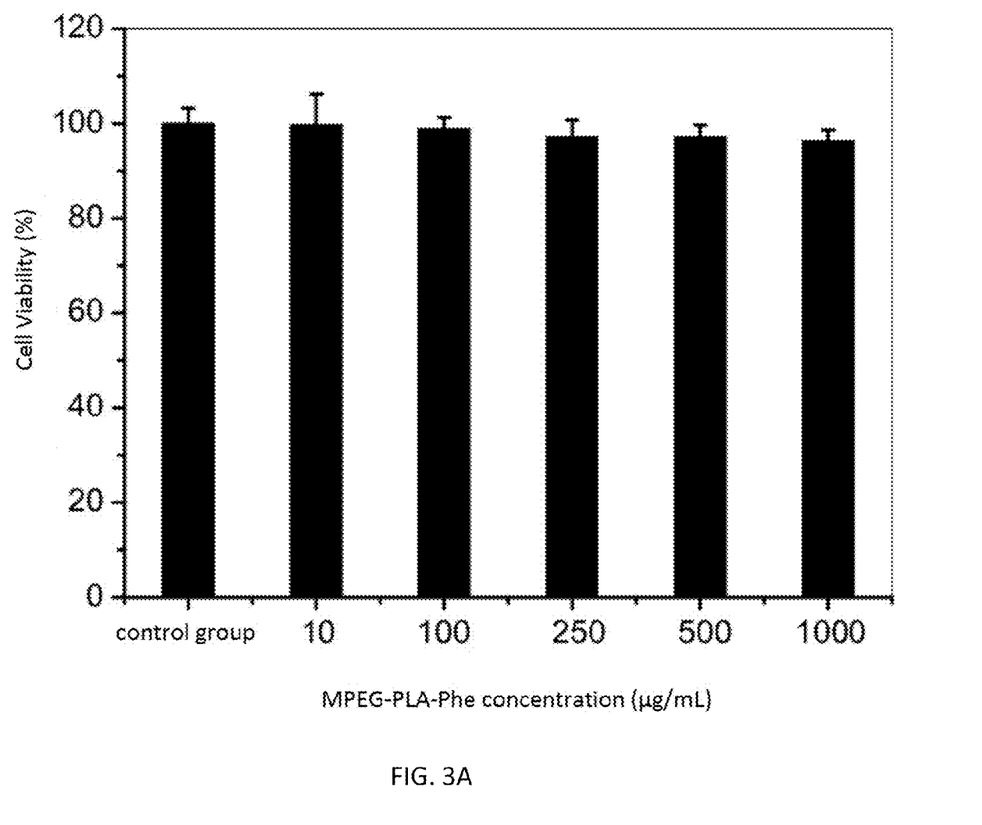
FIGS. 3A and 3B shows respectively the experimental results of cytotoxicity assay of block copolymer according to Example 1 and conventional MPEG-PLA.
Figure 3B:
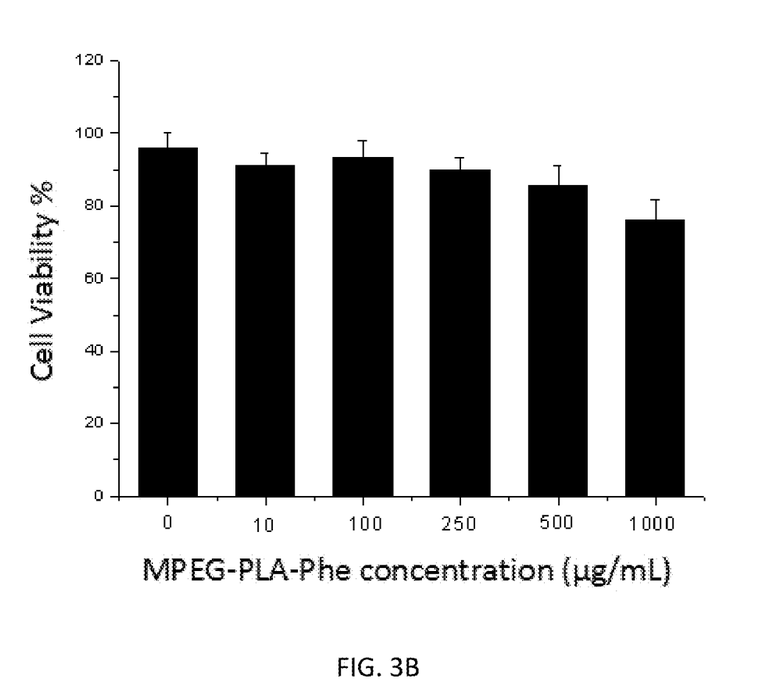

Specifically, the assay includes the following steps:

Firstly, culture L-02 cells (human hepatic cells) in DMEM medium with 10% fetal bovine serum (FBS), and seeding L-02 cells into a 96-well plate and further incubate for 24 hours. The methoxypoly(ethylene glycol)-poly(lactide) block copolymer capped with phenylalanine group is diluted and suspended in culture medium (DMEM medium with 10% FBS) in serial concentrations (10 to 1000 µg/mL). And the suspended medium are loading into the wells of the plate for further 24 hours of incubation. Then MTT assay is conducted to determine the cytotoxicity of the block copolymers. More specifically, the assay steps includes:

Load 180 µL of DMEM culture medium into each well, then add 20 µL/well of MTT solution, mix the mixture gently and incubate for 4 hours. Remove the medium containing MTT by suction and add 200 µL into each well. Put the plate on a shaker (set at 100 rpm) and incubate for 10 minutes at 37° C. Finally, measure the OD value at the absorbance at 570 nm by ELISA reader. Each of experiment is repeated for 6 times and the result of control group is defined as 100% of cell viability. The MPEG-PLA is also used for conducting MTT assay as described previously, and the effects of MPEG-PLA and MPEG-PLA-Phe on cell cytotoxicity are compared side by side, as shown in Table 1 and FIG. 3A and FIG. 3B. The OD values of the assay result are calculated to be expressed in percentage to determine the cell viability (%).

TABLE 1

| MPEG-PLA-Phe concentration (µg/mL) | Cell Viability % | Error % | MPEG-PLA concentration (µg/mL) | Cell Viability % | Error % |
| --- | --- | --- | --- | --- | --- |
| 0 | 100 | 3.23 | 0 | 96 | 4.22 |
| 10 | 99.72 | 6.53 | 10 | 91.24 | 3.25 |
| 100 | 98.95 | 2.32 | 100 | 93.41 | 4.77 |
| 250 | 97.23 | 3.51 | 250 | 90.07 | 3.34 |
| 500 | 97.16 | 2.53 | 500 | 85.45 | 5.72 |
| 1000 | 96.31 | 2.34 | 1000 | 76.28 | 5.28 |

In view of above results, the biocompatibility of the methoxypoly(ethylene glycol)-poly(lactide) block copolymer capped with phenylalanine group is superior to conventional MPEG-PLA without any amino acid cap, and this phenomenon is particularly significant when the MPEG-PLA and MPEG-PLA-Phe are assayed in high concentrations. Moreover, the biocompatibility of MPEG-PLA-Phe is superior than any of the known surfactant products. It is clear that the present invention provides an ideal solution of capping the block copolymers with an amino acid for greatly reducing the toxicity and improving biodegradability of the surfactant.

EXAMPLE 2

Preparation of a block copolymer capped with an amino acid group. Specifically, according to another embodiment of the present invention, the amino acid used is arginine, and thus the amino acid capping the block copolymer is derived from arginine. The block copolymer product according to Example 2 is called MPEG-PLA-Arg hereinafter.

MPEG-PLA is prepared as previously described in Example 1.

Weigh and dissolving 4 g of MPEG-PLA, 1.394 g of L-arginine, 0.19 g of condensing agents EDC (molar ratio is 1:3:1) in 50 mL distilled water. Adjust the pH value to 5.0 by using hydrochloric acid, and conduct the reaction at room temperature for 24 hours. Extract the reacted solution by 50 ml ethyl acetate repeatedly for 3 times, pool the organic phase and remove partial volume of the solvent, then precipitate the residual reacted solution by ethyl ether to obtain white solid, which is the desired product of MPEG-PLA-Arg. The yield is 4.06 g (90.9%).

The desired product of MPEG-PLA-Arg is characterized by NMR, IR and GPC methods, to determine their physical properties including spatial structure, monocular weight, and polydispersity. The results of structural characteristics of the desired product are respectively shown in FIG. 4.

Figure 4:
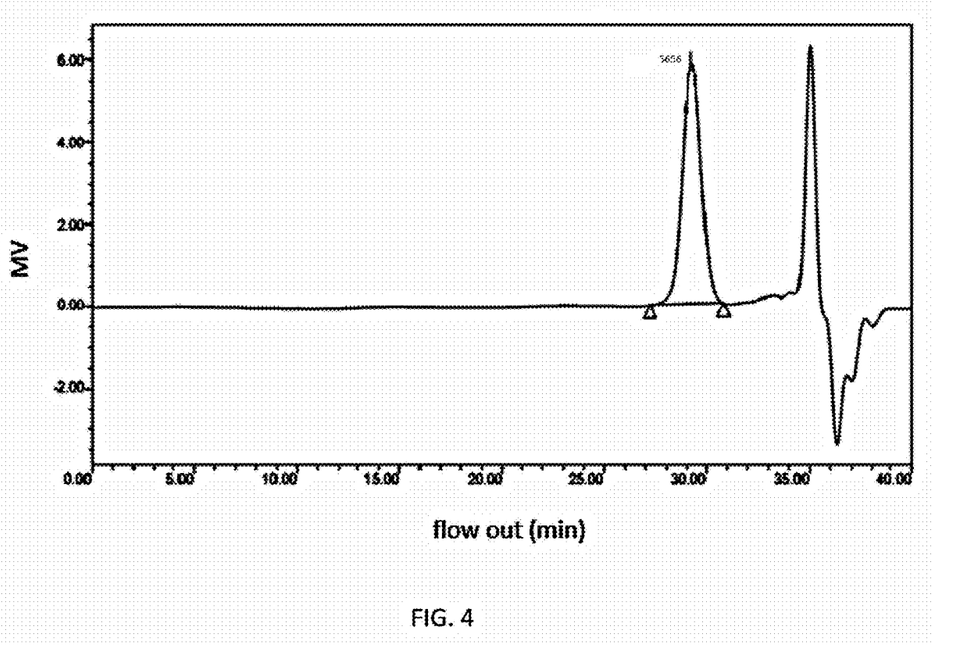
FIG. 4 is a gel permeation chromatography (GPC) chromatogram showing the distribution and the molecular weight of the block copolymer according to Example 2. The polydispersity index (PDI) is 1.05 and the peak shape is nearly symmetrical; both indicate excellent purity of the block copolymer.

According to the GPC results, the polydispersity index (PDI) of the desired product is 1.05 and the peak shape is nearly symmetrical, and those features indicate that the purity of the desired product is excellent.

To examine the surfactant property, add 60 mL water and 8 mL hexadecane into a 12-cm culture dish, and the hexadecane spreads and forms an oil film on the surface of water. Dissolve the quantified product of Example 2 in water to form a 20% of aqueous solution and then drop this solution into the center of the hexadecane oil film. It's observe that the oil spreads toward radially. This phenomenon demonstrates that the product obtained according to Example 2 has the feature of surfactant.

EXAMPLE 3

Preparation of a block copolymer capped with an amino acid group. Specifically, according to another embodiment of the present invention, the amino acid used is alanine, and thus the amino acid capping the block copolymer is derived from alanine. The block copolymer product according to Example 3 is called MPEG-PLA-Ala hereinafter.

MPEG-PLA is prepared as previously described in Example 1.

Weigh and dissolving 4 g of MPEG-PLA, 0.24 g of alanine, 0.19 g of condensing agents EDC (molar ratio is 1:3:1) in 50 mL distilled water. Adjust the pH value to 5.0 by using hydrochloric acid, and conduct the reaction at room temperature for 24 hours. Extract the reacted solution by 50 ml chloroform repeatedly for 3 times, pool the organic phase and remove partial volume of the solvent, then precipitate the residual reacted solution by ethyl ether to obtain white solid, which is the desired product of MPEG-PLA-Ala. The yield is 3.95 g (96.8%).

The desired product of MPEG-PLA-Ala is characterized by NMR, IR and GPC methods, to determine their physical properties including spatial structure, monocular weight, and polydispersity. The results of structural characteristics of the desired product are respectively shown in FIG. 5.

Figure 5:
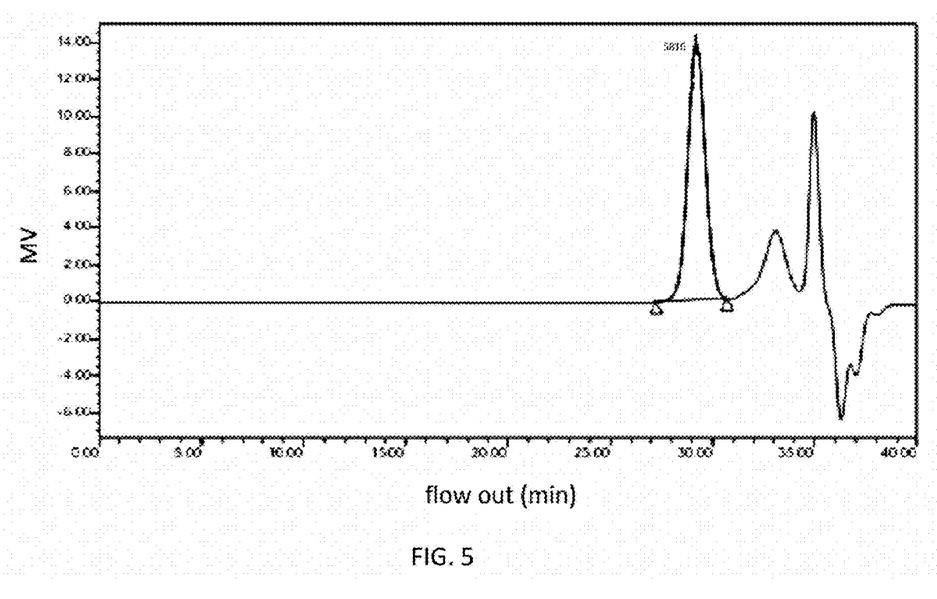
FIG. 5 is a gel permeation chromatography (GPC) chromatogram showing the distribution and the molecular weight of the block copolymer according to Example 3. The polydispersity index (PDI) is 1.05 and the peak shape is nearly symmetrical; both indicate excellent purity of the block copolymer.

According to the GPC results, the polydispersity index (PDI) of the desired product is 1.05 and the peak shape is nearly symmetrical, and those features indicate that the purity of the desired product is excellent.

To examine the surfactant property, add 60 mL water and 8 mL hexadecane into a 12-cm culture dish, and the hexadecane spreads and forms an oil film on the surface of water. Dissolve the quantified product of Example 2 in water to form a 15% of aqueous solution and then drop this solution into the center of the hexadecane oil film. It's observe that the oil spreads toward radially. This phenomenon demonstrates that the product obtained according to Example 2 has the feature of surfactant.

EXAMPLE 4

Formula of a specific face cleaner:

| Ingredient | Percentage (wt %) |
| --- | --- |
| MPEG-PLA-Phe [1] | 4.70% |
| pure water | 84.50% |
| ethanol | 4.50% |
| ethylene glycol | 2% |
| aloe extract [2] | 2% |

-continued

| Ingredient | Percentage (wt %) |
| --- | --- |
| PEG-6 caprylic/capric glycerides [3] | 2% |
| Allantoin | 0.30% |

[1] Refer to Example 1 for the synthetic process of MPEG-PLA-Phe
[2] Full name: *Aloe barbadensis* extract (CAS: 85507-69-3)
[3] CAS: 361459-38-3/8, manufactured by EVONIK-DEGUSSA (product name: TEGO-SOFT® GMC 6)

EXAMPLE 5

Formula of a specific shampoo:

| Ingredient | Percentage (wt %) |
| --- | --- |
| MPEG-PLA-Arg [4] | 28% |
| cocoamide DEA | 6% |
| methyl parahydroxybenzoate | 0.2% |
| propylparaben | 0.1% |
| parfum oil | 0.5% |
| vitamin E | 0.1% |
| vitamin C | 0.1% |
| Pure water | 65% |

[4] Refer to Example 2 for the synthetic process of MPEG-PLA-Arg

EXAMPLE 6

Formula of a specific body cleaner:

| Ingredient | Percentage (wt %) |
| --- | --- |
| MPEG-PLA-Ala [5] | 17% |
| disodium laureth sulfosuccinate | 14% |
| lauryl glucoside [6] | 17% |
| PEG-7 glyceryl cocoate [7] | 5% |
| sodium chloride | 3% |
| fragrance | 1% |
| pure water | 43% |

[5] Refer to Example 3 for the synthetic process of MPEG-PLA-Ala
[6] CAS: 110615-47-9, manufactured by Shanghai Fine Chemical Co. Ltd
[7] Supplier: GATTEFOSS (product name: GELUCIRE 44/14)

The above formulation examples show the use of the block copolymer according to the present invention for producing detergents. Based on the result of trial research performed on more than 100 subject users according to the Examples 4 to 6, the overall performance, including the cleaning capability and the skin comfort level, of the products formulated by the block copolymer according to the present invention is excellent; and is comparable to the currently popular commercial products, such as PANTENE, BEE FLOWER and T JOY. In view of the research result, in addition to the abovementioned advantageous characteristics (e.g., low toxicity and good biodegradability), the block copolymer according to the present invention can be widely used as a surfactant to be formulated in various cleaners to fully satisfy the demands of customers and earn more business opportunities.

Although the present invention has to disclose the preferred embodiment described above, the invention is not intended to be limited to the preferred embodiments described above. Any skilled in the art, without departing from the scope of the invention technical solutions circumstances, can make use of the above methods and techniques to reveal the contents of the invention and a number of possible technical solutions to make changes, modifications, replacements, combinations, and simplification on the present invention as equivalent embodiments. Therefore, all without departing from the contents of this practical new technical solution, based on a simple modification of the invention for any technical substance of the above embodiments made cases, equivalent variations and modifications as would fall within the scope of this invention.

What is claimed is:

1. A block copolymer having a methoxypoly(ethylene glycol) block component and a poly(lactide) block component, being capped with an amino acid group and being represented by formula (I) below:

wherein R represents an acyl amine group, and the formula (II) below:

wherein $R_1$ is $PhCH_2$, or $(CH_2)_3NHC(NH)NH_2$ and a is an integer of 20-200, and b is an integer of 5-50; the average molecular weight of the block copolymer ranging from 2000-20000; the average molecular weight a methoxypoly(ethylene glycol) block component ranging from 1000-5000; and the average molecular weight a poly(lactide) block component ranging from 1000-10000, wherein when methoxypoly(ethylene glycol) block component and a poly(lactide) block component in a concentration of 10-1000 μg/mL, the cell viability is detected by MTT method is greater than 95%.

2. The method of preparing a block copolymer as claimed in claim 1, wherein

R represents an acyl amine group, and the formula (II) below:

wherein $R_1$ is $PhCH_2$, or $(CH_2)_3NHC(NH)NH_2$ and a is an integer of 20-200, and b is an integer of 5-50; the average molecular weight of the block copolymer ranging from 2000-20000; the average molecular weight a methoxypoly(ethylene glycol) block component ranging from 1000-5000; and the average molecular weight a poly(lactide) block component ranging from 1000-10000; and the method comprises the steps of:

dissolving a methoxypoly(ethylene glycol)-poly(lactide) block copolymer and an amino acid in distilled water to form a working solution;

adding a condensing agent into the working solution for reaction at room temperature for 4 to 48 hours to obtain a product solution;

filtering the product solution to obtain a filtrate;

extracting the filtrate by using a polar organic solvent and precipitating the filtrate by a non-polar organic solvent to obtain a precipitation; and drying the precipitation to obtain the final product;

wherein the molar ratio of the methoxypoly(ethylene glycol)-poly(lactide) block copolymer: amino acid: condensing agent ranges from 1:1-10:0.1-10, wherein when methoxypoly(ethylene glycol) block component and a poly(lactide) block component in a concentration of 10-1000 μg/mL, the cell viability is detected by MTT method is greater than 95%.

3. The method as claimed in claim 2, wherein the block copolymer is prepared by the steps of:

adding methoxypoly(ethylene glycol) and D,L-Lactide together into a dry flask, wherein the weight ratio of methoxypoly(ethylene glycol) to D,L-Lactide is 1:1;

adding 0.1 g/mL of a stannous octoate dissolved in dichloromethane into the flask, wherein the weight of the stannous octoate dissolved in dichloromethane is 1/2000-1/500 to the weight of either methoxypoly (ethylene glycol) or D,L-Lactide to form a reaction mixture;

heating the reaction mixture to 80-100° C. to dissolve the methoxypoly(ethylene glycol);

stirring and vacuuming the reaction mixture for at least an hour, during which the atmosphere is replaced with nitrogen alternatively for 3 times;

sealing the flask in vacuum to perform a polymerization reaction at 130-150° C. in oil bath for 3.5-24 hours;

cooling the mixture and breaking the sealed flask to obtain a solid;

dissolving the solid with dichloromethane to form a crude solution, precipitating the crude solution with diethyl ether and filtering to obtain a precipitate; and drying the precipitate to obtain the desired block copolymer.

4. The method as claimed in claim 2, wherein the molar ratio of the methoxypoly(ethylene glycol)-poly(lactide) block copolymer:amino acid: condensing agent ranges from 1:3:1.

5. The method as claimed in claim 2, wherein the polar organic solvent is selected from the group consisting of methanol, chloroform and tetrahydrofuran.

6. The method as claimed in claim 2, wherein the non-polar organic solvent is selected form the group consisting of petroleum ether and n-hexane.

7. A use of a block copolymer as claimed in claim 1, for a surfactant.

8. The method as claimed in claim 2, wherein the condensing agent is 3-(ethyliminomethyleneamino)-N,N-dimethyl-propan-1-amine.

* * * * *